(12) United States Patent
Mitchell

(10) Patent No.: US 7,872,635 B2
(45) Date of Patent: Jan. 18, 2011

(54) FOVEATED DISPLAY EYE-TRACKING SYSTEM AND METHOD

(75) Inventor: Brian T. Mitchell, Swartz Creek, MI (US)

(73) Assignee: Optimetrics, Inc., Ann Arbor, MI (US)

( * ) Notice: Subject to any disclaimer, the term of this patent is extended or adjusted under 35 U.S.C. 154(b) by 1085 days.

(21) Appl. No.: 10/846,035

(22) Filed: May 14, 2004

(65) Prior Publication Data

US 2004/0227699 A1    Nov. 18, 2004

Related U.S. Application Data

(60) Provisional application No. 60/470,940, filed on May 15, 2003.

(51) Int. Cl.
*G09G 3/06* (2006.01)
*G06F 3/033* (2006.01)

(52) U.S. Cl. .......................... 345/158; 345/44
(58) Field of Classification Search ............ 345/44, 345/158

See application file for complete search history.

(56) References Cited

U.S. PATENT DOCUMENTS

| | | | |
|---|---|---|---|
| 3,983,474 A | 9/1976 | Kuipers | 324/43 R |
| 4,102,564 A | 7/1978 | Michael | 351/7 |
| 4,373,787 A | 2/1983 | Crane et al. | 351/210 |
| 4,568,159 A | 2/1986 | Baldwin | 351/210 |
| 4,582,403 A | 4/1986 | Weinblatt | 351/210 |
| 4,585,011 A | 4/1986 | Broughton et al. | 128/733 |
| 4,634,384 A | 1/1987 | Neves et al. | 434/44 |
| 4,648,052 A | 3/1987 | Friedman et al. | 364/550 |
| 4,659,197 A | 4/1987 | Weinblatt | 351/210 |
| 4,702,575 A | 10/1987 | Breglia | 351/210 |
| 4,720,189 A | 1/1988 | Heynen et al. | 351/210 |
| 4,729,652 A | 3/1988 | Effert | 351/210 |
| 4,735,498 A | 4/1988 | Udden et al. | 351/210 |
| 4,798,214 A | 1/1989 | Haas | 128/745 |
| 4,836,670 A | 6/1989 | Hutchinson | 351/210 |
| 4,848,340 A | 7/1989 | Bille et al. | 128/303.1 |
| 4,852,988 A | 8/1989 | Velez et al. | 351/210 |
| 4,958,925 A | 9/1990 | Ober et al. | 351/210 |
| 4,973,149 A | 11/1990 | Hutchinson | 351/210 |
| 4,988,183 A | 1/1991 | Kasahara et al. | 351/210 |
| 5,002,384 A | 3/1991 | Trachtman | 351/203 |

(Continued)

OTHER PUBLICATIONS

Anthony Jansen, Alan Blackwell and Kim Marriott, "A tool for tracking visual attention: The Restricted Focus Viewer", Feb. 1, 2003, Behavior Research Methods, Instruments, & Computers, vol. 35, No. 1, pp. 57-69.*

(Continued)

*Primary Examiner*—Amr Awad
*Assistant Examiner*—Randal Willis
(74) *Attorney, Agent, or Firm*—Gifford, Krass, Sprinkle, Anderson & Citkowski, P.C.

(57) ABSTRACT

A system for detecting and recording eye-tracking data by presenting to an observer a display image with an area in focus surrounded by blurred areas. The observer may shift the focus area within the image by head movements which are wirelessly transmitted to a receiver and used to modify the displayed image. This system solves that part of the eye-tracking problem that is most critical for measuring cognitive processes.

2 Claims, 2 Drawing Sheets

U.S. PATENT DOCUMENTS

| | | | | |
|---|---|---|---|---|
| 5,093,567 | A | 3/1992 | Staveley | 250/221 |
| 5,094,521 | A | 3/1992 | Jolson et al. | 351/210 |
| 5,106,184 | A | 4/1992 | Milbocker | 351/221 |
| 5,150,137 | A | 9/1992 | Owens, II et al. | 351/210 |
| 5,155,516 | A | 10/1992 | Shindo | 354/219 |
| 5,196,873 | A | 3/1993 | Yamanobe et al. | 351/210 |
| 5,212,506 | A | 5/1993 | Yoshimatsu et al. | 351/210 |
| 5,214,455 | A | 5/1993 | Penney et al. | 351/210 |
| 5,218,387 | A | 6/1993 | Ueno et al. | 351/210 |
| 5,220,361 | A | 6/1993 | Lehmer et al. | 351/226 |
| 5,231,674 | A | 7/1993 | Cleveland et al. | 382/6 |
| 5,260,734 | A | 11/1993 | Shindo | 354/219 |
| 5,262,807 | A | 11/1993 | Shindo | 351/210 |
| 5,270,748 | A | 12/1993 | Katz | 351/210 |
| 5,293,187 | A | 3/1994 | Knapp et al. | 351/210 |
| 5,307,072 | A | 4/1994 | Jones, Jr. | 342/147 |
| 5,345,281 | A | 9/1994 | Taboada et al. | 351/210 |
| 5,367,315 | A | 11/1994 | Pan | 345/156 |
| 5,373,857 | A | 12/1994 | Travers et al. | 128/782 |
| 5,382,989 | A | 1/1995 | Uomori et al. | 351/209 |
| 5,386,258 | A | 1/1995 | Nagano | 354/400 |
| 5,408,292 | A | 4/1995 | Kumakura | 354/410 |
| 5,410,376 | A | 4/1995 | Cornsweet et al. | 351/210 |
| 5,416,317 | A | 5/1995 | Nishimura et al. | 250/221 |
| 5,424,556 | A | 6/1995 | Symosek et al. | 250/561 |
| 5,428,413 | A | 6/1995 | Shindo | 351/210 |
| 5,430,505 | A | 7/1995 | Katz | 351/208 |
| 5,453,686 | A | 9/1995 | Anderson | 324/207 |
| 5,467,777 | A | 11/1995 | Farwell | 128/731 |
| 5,471,542 | A | 11/1995 | Ragland | 382/128 |
| 5,481,622 | A | 1/1996 | Gerhardt et al. | 382/103 |
| 5,491,492 | A | 2/1996 | Knapp et al. | 345/8 |
| 5,517,021 | A | 5/1996 | Kaufman et al. | 250/221 |
| 5,532,784 | A | 7/1996 | Nishimura et al. | 354/410 |
| 5,552,854 | A | 9/1996 | Nishimura | 354/410 |
| 5,555,895 | A | 9/1996 | Ulmer et al. | 128/782 |
| 5,583,335 | A | 12/1996 | Spitzer et al. | 250/221 |
| 5,583,795 | A | 12/1996 | Smyth | 364/516 |
| 5,604,818 | A | 2/1997 | Saitou et al. | 382/128 |
| 5,608,489 | A | 3/1997 | Ozaki | 396/51 |
| 5,610,673 | A | 3/1997 | Rafal et al. | 351/210 |
| 5,614,967 | A | 3/1997 | Ishikawa et al. | 351/210 |
| 5,632,742 | A | 5/1997 | Frey et al. | 606/12 |
| 5,638,176 | A | 6/1997 | Hobbs et al. | 356/355 |
| 5,640,170 | A | 6/1997 | Anderson | 343/895 |
| 5,686,940 | A * | 11/1997 | Kuga | 345/156 |
| 5,689,619 | A | 11/1997 | Smyth | 395/10 |
| 5,726,916 | A | 3/1998 | Smyth | 364/559 |
| 5,731,805 | A | 3/1998 | Tognazzini et al. | 345/156 |
| 5,765,045 | A | 6/1998 | Takagi et al. | 396/51 |
| 5,831,594 | A | 11/1998 | Tognazzini et al. | 345/156 |
| 5,844,544 | A | 12/1998 | Kahn et al. | 345/156 |
| 5,857,120 | A | 1/1999 | Konishi | 396/51 |
| 5,861,940 | A | 1/1999 | Robinson et al. | 351/221 |
| 5,880,812 | A | 3/1999 | Solomon | 351/210 |
| 5,892,566 | A | 4/1999 | Bullwinkel | 351/210 |
| 5,898,423 | A | 4/1999 | Tognazzini et al. | 345/158 |
| 5,898,474 | A | 4/1999 | McClure et al. | 351/224 |
| 5,912,721 | A | 6/1999 | Yamaguchi et al. | 351/210 |
| 5,966,197 | A | 10/1999 | Yee | 351/210 |
| 5,973,737 | A | 10/1999 | Yokota | 348/209 |
| 5,980,041 | A | 11/1999 | Strachan | 351/210 |
| 5,987,151 | A | 11/1999 | Akashi | 382/100 |
| 6,009,210 | A | 12/1999 | Kang | 382/276 |
| 6,027,216 | A | 2/2000 | Guyton et al. | 351/200 |
| 6,033,073 | A | 3/2000 | Potapova et al. | 351/211 |
| 6,036,316 | A | 3/2000 | Arita | 351/210 |
| 6,079,829 | A | 6/2000 | Bullwinkel | 351/210 |
| 6,084,556 | A | 7/2000 | Zwern | 345/209 |
| 6,090,051 | A | 7/2000 | Marshall | 600/558 |
| 6,091,378 | A | 7/2000 | Richardson et al. | 345/209 |
| 6,102,870 | A | 8/2000 | Edwards | 600/558 |
| 6,106,119 | A | 8/2000 | Edwards | 351/209 |
| 6,120,461 | A | 9/2000 | Smyth | 600/558 |
| 6,127,990 | A | 10/2000 | Zwern | 345/8 |
| 6,152,563 | A | 11/2000 | Hutchinson et al. | 351/209 |
| 6,160,536 | A | 12/2000 | Forest | 345/157 |
| 6,182,114 | B1 | 1/2001 | Yap et al. | 709/203 |
| 6,184,847 | B1 | 2/2001 | Fateh et al. | 345/8 |
| 6,204,828 | B1 * | 3/2001 | Amir et al. | 345/7 |
| 6,231,187 | B1 | 5/2001 | Munoz et al. | 351/209 |
| 6,252,989 | B1 | 6/2001 | Geisler et al. | 382/232 |
| 6,283,954 | B1 | 9/2001 | Yee | 606/5 |
| 6,299,307 | B1 | 10/2001 | Oltean et al. | 351/210 |
| 6,299,308 | B1 | 10/2001 | Voronka et al. | 351/210 |
| 6,307,526 | B1 | 10/2001 | Mann | 345/8 |
| 6,317,103 | B1 | 11/2001 | Furness, III et al. | 345/8 |
| 6,351,273 | B1 | 2/2002 | Lemelson et al. | 345/786 |
| 6,351,335 | B1 | 2/2002 | Perlin | 359/618 |
| 6,359,601 | B1 | 3/2002 | Maguire, Jr. | 345/7 |
| 6,359,603 | B1 | 3/2002 | Zwern | 345/8 |
| 6,369,564 | B1 | 4/2002 | Khalfin et al. | 324/207 |
| 6,373,961 | B1 | 4/2002 | Richardson et al. | 382/103 |
| 6,377,295 | B1 | 4/2002 | Woodgate et al. | 348/59 |
| 6,377,401 | B1 | 4/2002 | Bartlett | 359/630 |
| 6,400,139 | B1 | 6/2002 | Khalfin et al. | 324/207.17 |
| 6,421,185 | B1 | 7/2002 | Wick et al. | 359/637 |
| 6,433,759 | B1 | 8/2002 | Richardson et al. | 345/7 |
| 6,433,760 | B1 | 8/2002 | Vaissie et al. | 345/8 |
| 6,445,364 | B2 | 9/2002 | Zwern | 345/8 |
| 6,456,262 | B1 | 9/2002 | Bell | 345/8 |
| 6,459,446 | B1 | 10/2002 | Harman | 348/51 |
| 6,473,241 | B1 | 10/2002 | Wick et al. | 359/637 |
| 6,507,702 | B2 | 1/2003 | Ohtani | 396/50 |
| 6,526,159 | B1 | 2/2003 | Nickerson | 382/117 |
| 6,542,081 | B2 | 4/2003 | Torch | 340/575 |
| 6,545,664 | B1 * | 4/2003 | Kim | 345/158 |
| 6,568,808 | B2 | 5/2003 | Campin | 351/209 |
| 6,594,687 | B1 | 7/2003 | Yap et al. | 709/203 |
| 6,670,963 | B2 | 12/2003 | Osberger | 345/629 |
| 2002/0180799 | A1 | 12/2002 | Peck et al. | 345/784 |
| 2003/0067476 | A1 | 4/2003 | Miller et al. | 345/598 |

OTHER PUBLICATIONS

S.B. Kang, "Hands-Free Navigation in VR Environments by Tracking the Head," Mar. 1997.

R. Kijima, T. Ojika; "Reflex HMD to Compensate Lag and Correction of Derivative Deformation," (date unknown).

* cited by examiner

FOVEATED DISPLAY EYE-TRACKING SYSTEM AND METHOD

REFERENCE TO RELATED APPLICATION

This application claims priority from U.S. Provisional Patent Application Ser. No. 60/470,940, filed May 15, 2003, the entire content of which is incorporated herein by reference.

FIELD OF THE INVENTION

This invention relates to a system and method for analyzing and recording the eye movement of a subject exposed to a display of an image, and more particularly, to such a system in which the display image has a foveated region and a non-foveated region and the system detects head movement of the subject to move the foveated region within the image.

BACKGROUND OF THE INVENTION

There is little doubt that eye-tracking provides valuable insight into the current mental state and problem solving strategy of a human subject. The human retina is anisotropic, and has a high-resolution fovea surrounded by a much lower resolution peripheral retina. In order for this architecture to work properly, the eyes must move rapidly about the scene. The net effect of this movement, is the illusion that the human vision system (HVS) has both a large field-of-view and a high acuity across the entire visual field. What is actually happening, however, is that the rapid movements of the eye are sequentially capturing the information needed to solve a particular problem. It is the fact that eyes acquire information in small amounts and in a sequential manner that makes eye-tracking so important to understanding the state of the human subject. It is the only tool that allows a researcher to explore the portions of the cognitive process that cannot be articulated.

The research literature is filled with eye-tracking studies that validate that statement, and illustrate that eye-tracking can be used to measure learning. For example, eye-tracking was used to show strategic game playing differences between novice and expert players of the game Tetris. As reported, expert players do not play the game faster than novice players. Quite the contrary. Experts stretch out the placement of the current piece for as long as possible so that they can concentrate on where to place the next piece. This is actually a clever strategy that maximizes decision time. Although the expert player could not articulate this strategy, it was clearly evident in the eye movement histories. The novice player simply focused on placing the current piece, and in fact, played the game at a much faster rate than the expert. This simple example illustrates the power that eye-tracking has on uncovering non-intuitive problem solving strategies and the potential that eye-tracking has for developing measures of performance and training methods.

Although current methods of eye-tracking have demonstrated tremendous potential for the use of this data, they have fallen short in their overall ability to facilitate widespread use of this technology for training. Many of these methods capture and process a video stream of the working eye, and require extensive image processing methods to obtain eye position information. Unfortunately, these contemporary eye-trackers fall short of perfection, and as a result, they have received much criticism: they are too expensive, they are too difficult or cumbersome to wear, they are too hard to use, a chin rest or bite bar may be required to restrict head movement, they do not work for individuals that wear glasses or contact lenses, they require frequent calibrations and recalibrations, and the data they collect can be corrupted by blinks or glances.

In short, current eye-tracking methods are far from perfect, and none of the current devices completely satisfy all the requirements identified for an ideal eye-tracker. Alternative approaches to eye-tracking based on video oculography (VOG), infrared oculography (IROG), and electro-oculography (EOG) methods have also been developed.

The VOG approach relies on determining the relative position of the subject's cornea and a glint of infrared light reflected off the pupil. An infrared emitter is used to produce the glint and a video camera is used to capture a sequence of images that contain the glint and subject's eye. Image processing techniques are used to determine the position of the cornea and the glint. The position of the glint relative to the cornea changes as the eye moves. Thus, a VOG-based eye-tracker calculates eye position based on the relative position of the cornea and the reflected pupil glint. In general, this method of eye-tracking requires an infrared emitter and a video camera mounted to maintain a fixed relationship to the subject's eye that often results in cumbersome and expensive eye-tracking devices. This method has good spatial and temporal resolution, but head movements and eye blinks can effect image quality and tracking performance.

The IROG approach relies on measuring the intensity of infrared light reflected back from the subject's eye. Infrared emitters and infrared detectors are located in fixed positions around the eye. The amount of light reflected back to a fixed detector varies with eye position. Thus, an IROG-based eye-tracker calculates eye position based on the amount of reflected infrared light. In general, this method of eye-tracking requires goggles with mounted infrared emitters and detectors, and such devices are often both intrusive and expensive. This method has good spatial resolution and high temporal resolution, but is better for measuring horizontal than vertical eye movements and has difficulty with eye blinks which alter the amount of reflected light.

The EOG approach relies on the fact that the eye has a standing electrical potential across it with the front of the eye positive and the back of the eye negative. This potential varies from one to several millivolts, depending on the individual and illumination levels. EOG is measured by placing electrodes above and below the eye and on the outside of each eye. Changes in the EOG signals are directly related to changes in eye position. Thus, an EOG-based eye-tracker calculates eye position based on these signals. In general, this method of eye-tracking requires extensive calibration and lacks the precision needed for many eye-tracking applications. Foveated or gaze-contingent variable-resolution displays have been well developed in previous works. Foveated display techniques select the foveated region by actively tracking the subject's eyes and presenting an area of high spatial resolution at the point of gaze. Widespread application of such displays has been slowed by several difficulties. The technique requires fast and continuous tracking of the gaze point, and previous eyetrackers have been too expensive for widespread application, too imprecise, or too invasive for routine use. At present, the widespread use of gaze-contingent applications depends primarily on the development of low-cost eye-tracking systems.

SUMMARY OF THE INVENTION

The present invention relates to a new approach to eye-tracking. This approach simplifies the eye-tracking problem by using simple head movements, other body cues, or a combination of head and other body cues to control a foveated display. In a preferred embodiment of the invention, which will subsequently be disclosed in detail, the foveated region of the display is presented in-focus. The remainder of the display is blurred to correspond to the peripheral field of view found in the HVS. Head movements are used to move the foveated region within the field of view. Movements of the subject's head are detected and operate through the display system to change the foveated region of the image so that the subject acquires visual information by moving the foveated region through a series of head movements. The foveated region movements correspond to eye movements and may be recorded for subsequent analysis.

The benefits of this approach are significant. Gaze-point tracking simply becomes a matter of following the foveated region on the display. Not only is this simple to calculate, but it is more precise. Since the exact location of the fovea is known, this solution offers more precise calculation of the gaze point than conventional methods. It eliminates many of the calibration and recalibration issues normally associated with eye-tracker equipment, it is also less expensive. Since the gaze point corresponds to the display position of the foveal region, no calculations are needed to translate gaze point to screen coordinates. No optics or video cameras are required. Instead, a simple control device based on body motion is used to move the foveated region on the display screen, in short, the proposed method is more precise, easier to use, and less expensive than current methods.

While the preferred embodiment of the present invention uses head motion to control the foveated region, it might be possible in other embodiments to detect other body movement cues or combined head and other body cues to control the foveated display.

The system of the present invention requires a close correlation between head movement and eye movement. It is possible to move the eyes without moving the head, but the subject must make an effort to move the head to reposition the eyes. The user will learn the eye-head relationship over time through perceptual feedback provided through the foveated region placement.

Once learned, the position of the foveated region will correspond to eye gaze point, and the entire system will be perceptually seamless to the user. While the user may be initially drawn toward eye movement without head movement, since this will not change the in-focus area on the displayed image, the user will quickly learn that head movements are required to acquire information from the image.

Rather than explicitly measuring the position or orientation of the eye, the foveated display eye-tracker invention (FD eye-tracker) relies on a control strategy that works in concert with the head-eye control mechanism to move a foveated region on a computer screen. The idea is that the foveated display provides the same mechanism for acquiring visual information as the Human Vision System (HVS); a region of high-resolution must be sequentially moved around in the field of view at a rapid rate so that the human can obtain a complete understanding of the scene. By combining this approach with the natural head-eye control system of the Human Vision System, a device can be produced that would allow simple recording of the foveal position. Such a device would mirror the mechanism that the HVS uses to collect information, and would be controlled by an augmented version of the HVS head-eye control system.

BRIEF DESCRIPTION OF THE DRAWINGS

Other objects, advantages and applications of the present invention will be made apparent by the following detailed description of a preferred embodiment of the invention. The description makes reference to the accompanying drawings in which.

DETAILED DESCRIPTION OF THE INVENTION

Figure 1:
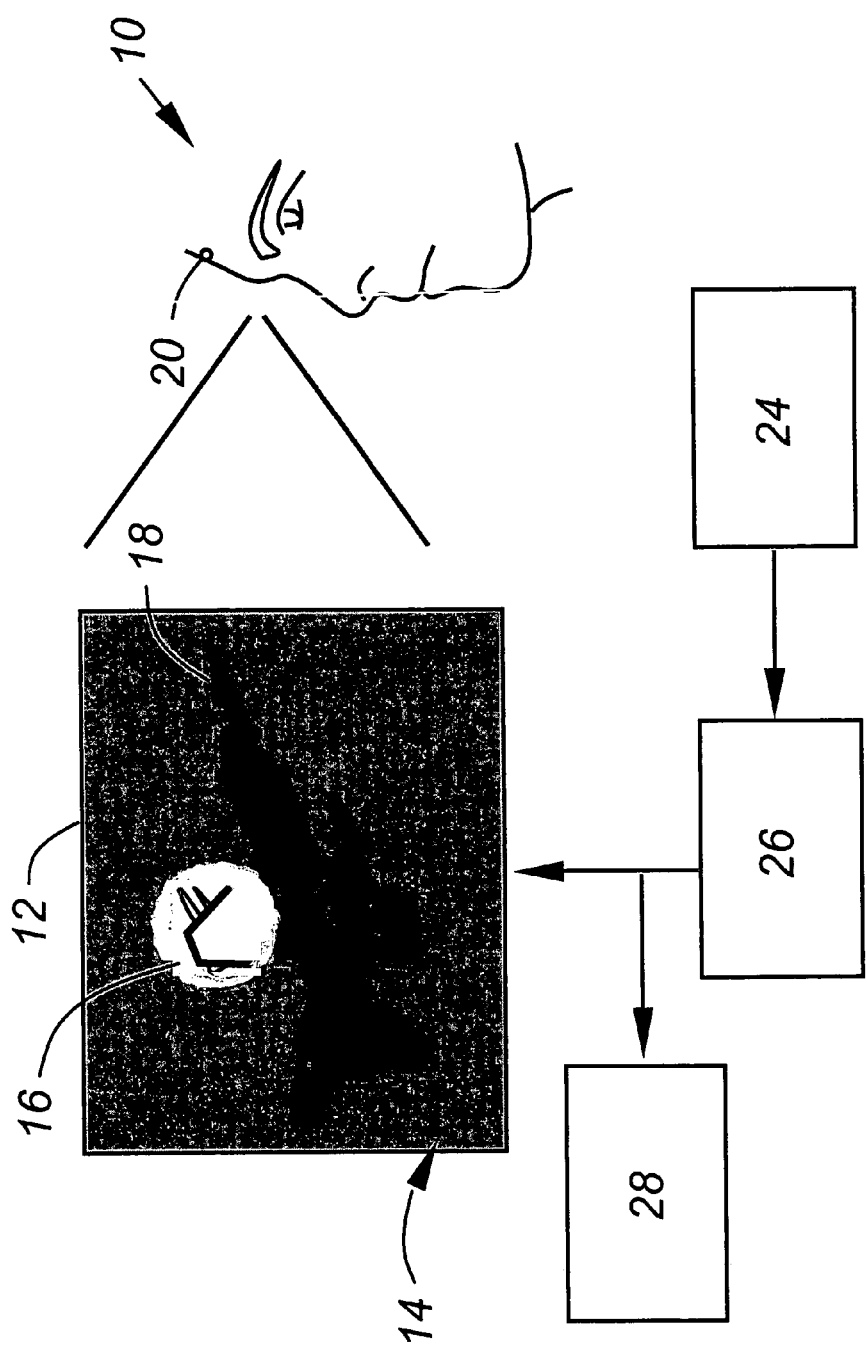
FIG. 1 is a schematic view of a user gazing at a display screen of a foveated image and having head tracking apparatus to position the foveated region and record the movements that correspond to eye position.

FIG. 1 is a schematic drawing of a subject generally indicated at 10, using the system of the present invention by observing a foveated display on a screen 12 such as a computer display screen. The image 14 displayed on the screen 12 has an area 16 that is in-focus and other areas 18 that are blurred. In the preferred embodiment, the foveated region 16 is circular in shape to correspond to the human retina. The subject 10 is positioned and directed so that the movement of the eyes to acquire visual information from the foveated image 14 is achieved by motions of the head which move the area 16.

The subject's head has a motion transmitter 20 attached. The signals generated by the transmitter 20 as the head moves, are picked up by a wireless receiver 24. The output of the receiver is provided to a foveated display generator 26. The foveated display generator 26 produces the image 14 with an in-focus area 16 surrounded by areas 18 that are blurred and moves the in-focus area 16 with respect to the general image, as a function of the detected head movements. In-focus area 16 positions are provided to a recorder 28.

The head tracker, generally including a transmitter 20 and a receiver 24, may take the form of any one of a variety of commercially available systems. One group of these head trackers is used to give disabled users control of the mouse function on a personal computer. These systems are generally low in cost and are directly applicable to the present invention. For example, the HeadMouse sold by Origin Instruments Corporation of Grand Prairie, Tex., would be useful with the present invention. It incorporates a small, flexible, paper-thin tracking dot typically attached to the forehead of the user and a receiver which detects the position of the dot using near-infrared signals.

Figure 2A:
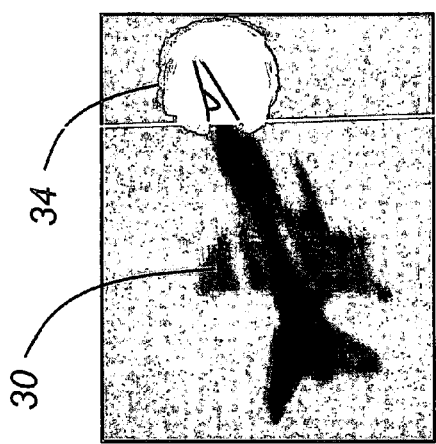
FIGS. 2A and 2B are displays of a foveated image with different areas displayed in high-resolution.
Figure 2B:
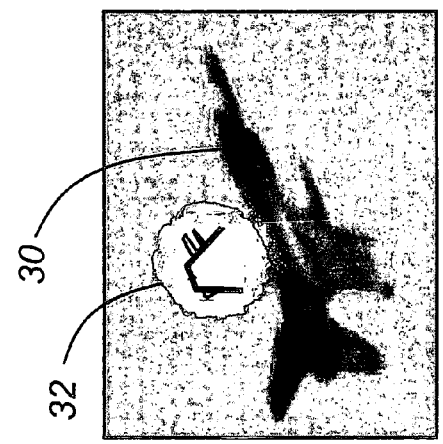
Figure 3:
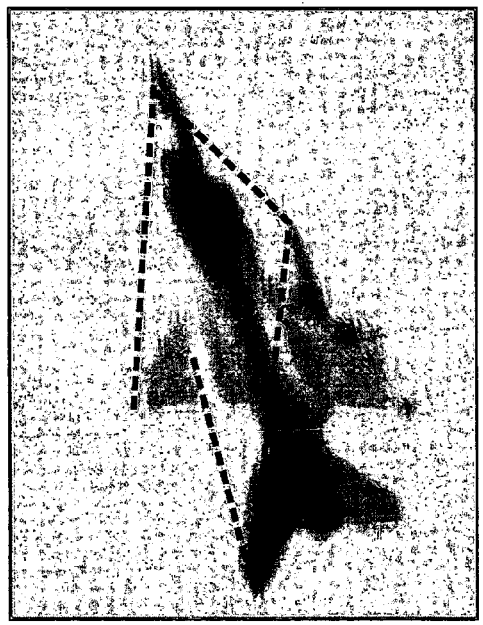
FIG. 3 is a scanpath graph of the eye movements of the subject as the eyes are moved from the position that corresponds to the image in FIG. 2A to the position that corresponds to the image in FIG. 2B.

FIGS. 2A and 2B represent displays of an image, generally indicated at 30 in both views, in which different areas of the image are displayed in-focus: the area 32 in FIG. 2A and the area 34 in FIG. 2B. The balance of both images are blurred. By movements of the head of the subject 10, the subject can shift the in-focus area to acquire information of the image. Those movements are recorded on a recorder 28 and may be played back in super position to the image 30, shown in FIG. 3, in which the entire image 30 is shown in-focus and the scanpath 36 used by the subject 10 to gain information of the image is superimposed on the image 30.

The image generated may be of the type disclosed in an article by Jansen, A. R., Blackwell, A. F., and Marriott, K., "A Tool for Tracking Visual Attention: The Restricted Focus Viewer," Behavioral Research Methods Instruments and Computers, 35(1): 57-69, February 2003. The system disclosed in this paper has a functional goal similar to that disclosed herein, but operates in an entirely different manner, with the user moving a mouse to change the region in focus of a foveated image. The foveal display technique found in the restricted focus viewer (described in that paper) may be used with the present invention for the display unit 26, with the head motion receiver 24 of the present invention and a control system that mirrors the control system of the human vision system substituting for the mouse. The referenced paper describes a method of generating a graded, blurring effect about the central, in-focus portion of the foveated image, which is useful with the present invention.

The images 30 which may be displayed and used for detecting eye tracking through head tracking with the present invention are not limited to static images and may include moving images such as streaming video, motion pictures, and computer-generated video streams dynamically produced from computer applications.

The inventive system and method disclosed herein may be used with other methodologies to improve performance. For example, ancillary data such as EOG or other data may be combined with head movements to control the foveated region. The FD data may be time-synchronized with FD position, to produce a form of FD position time-stamping, and a sequence of FD points, such as those shown in FIG. 3, may be processed or post-processed for analysis purposes.

The FD position may coincide with a comfortable head position upon initialization. For example, the initialization of the FD position may appear in the center of the screen, or precisely at eye level. During initialization a comfortable relationship between the foveal display region and the user's head alignment is established before commencing movement of the foveal region. This is accomplished by displaying the foveal region in the center of the screen, aligning the user's head in a comfortable position with respect to that position of the foveal region, and then commencing movement of the foveal region as determined by subsequent head movements.

The foveal region may also be parameterized to allow for varying viewing distances, and a calculation may be used with respect to the distance between the head and the display to change the foveated region display characteristics to mirror those associated with HVS perceptual capabilities. The method used to parameterize the foveal region for viewing distance may be of the type disclosed in an article by T. Kuyel, W. S. Geisler and J. Ghosh, "Retinally reconstructed images: Digital images having a resolution match with the human eye", IEEE Trans. Systems, Man and Cybernetics—Part A, 29(2), March 1999, pp. 235-243. The viewing distance between computer display and user's eyes may be dynamically calculated from the signals generated by the transmitter 20 as the head moves and received by the wireless receiver 24 using well-known methods such as triangulation or time-of-flight. The resulting distance can be used to dynamically modify the viewing characteristics of the foveated region to correspond to HVS perceptual capabilities.

A foveated display eye-tracker with no perceptual side effects has many positive attributes. Such a device would be relatively inexpensive, easy to use, produce very precise data, and be minimally invasive. It has all the qualities that the current technology does not. The FD eye-tracker is not ideal. It does, however, provide a set of qualities that would enable widespread use of the device for training and other applications.

The method of this invention preserves the portion of eye-tracking that provides a glimpse into cognitive processes (sequential visual data acquisition), and, as such, it creates a tool for understanding cognitive performance levels. Thus, even though it only solves a part of the eye-tracking problem in general, it only solves a part that is most critical for measuring cognitive processes. Accordingly, the system and method find numerous applications, including the ability to determine cognitive workload control over human-computer interaction. Human performance may be analyzed in these reactions, or real-world tasks may be simulated and analyzed in conjunction with the system and method.

For the military and commercial markets, such a device has the potential to revolutionize the methods by which individuals are trained to operate high-performance systems. Modern military systems require advanced training methods that assure the cognitive readiness of our warfighters. Achieving cognitive readiness is important for the following reasons; 1) the warfighter is mentally prepared, 2) the warfighter is performing at an optimal level, 3) the tools and techniques for training the warfighter are the most effective and affordable, and 4) the tools and techniques that the warfighter uses are the most effective and affordable. Because the post-Cold War challenges include the potential of simultaneous, multiple, geographically separate, high- or low-intensity conflicts, as well as peacekeeping, counter-terrorism, and disaster support missions, training for such diverse threats has the potential to strain limited resources. This, coupled with the increasing complexity of modern warfare techniques, has placed an increasing importance on developing training techniques that maximize the use of resources. This invention may be used to obtain a quick snapshot of student capabilities so that optimal training techniques can be prescribed. Thus, the disclosed eye-tracker has the potential to revolutionize the method in which modern warfighters are trained.

Within the commercial markets, the eye-tracker could support the development of products in such areas as advanced training, telemedicine, remote vehicle operation, and video teleconferencing.

I claim:

1. An eye-tracking method, comprising the steps of:
generating an image in which a selected foveated region is more focused than the balance of the image;
displaying the generated image to a user;
tracking movements of the user's head;
changing the area of the image which mirrors user eye movement and is in-focus relative to the balance of the image as a function of the user's head movements to obtain information about the image;
recording the movements of the position of the in-focus area on the display screen while acquiring information from the image; and
using combined head movement data and eyetracking or EOG derived data to control the foveated region.

2. An eye-tracking method, comprising the steps of:
generating an image in which a selected foveated region is more focused than the balance of the image;
displaying the generated image to a user;
tracking movements of the user's head;
changing the area of the image which mirrors user eye movement and is in-focus relative to the balance of the image as a function of the user's head movements to obtain information about the image;
recording the movements of the position of the in-focus area on the display screen while acquiring information from the image; and
time-synchronizing the foveated region to minor user eye movement as a function of combined eye and head position data.

* * * * *